US006340457B1

(12) United States Patent
Andriolli et al.

(10) Patent No.: US 6,340,457 B1
(45) Date of Patent: Jan. 22, 2002

(54) PHARMACEUTICAL AND ALIMENTARY COMPOSITIONS CONTAINING BACTERIA OF GENUS ACETOBACTER

(75) Inventors: Adriano Andriolli; Fausto Panni, both of Milan (IT)

(73) Assignee: Farmilia Farmaceutici Milano S.R.L., Settimo Milanese (IT)

( * ) Notice: Subject to any disclaimer, the term of this patent is extended or adjusted under 35 U.S.C. 154(b) by 0 days.

(21) Appl. No.: 09/341,389

(22) PCT Filed: Jan. 5, 1998

(86) PCT No.: PCT/EP98/00019

§ 371 Date: Aug. 2, 1999

§ 102(e) Date: Aug. 2, 1999

(87) PCT Pub. No.: WO98/30226

PCT Pub. Date: Jul. 16, 1998

(30) Foreign Application Priority Data

Jan. 8, 1997 (IT) .......................................... MI97A0013

(51) Int. Cl.⁷ .......................... A61K 35/74; A61K 9/48; A61K 9/02
(52) U.S. Cl. ...................... 424/93.4; 424/436; 424/451; 426/61; 426/71; 426/658; 435/252.1; 435/823

(58) Field of Search ............................ 426/71, 658, 61; 424/451, 436, 93.4; 435/252.1, 823

(56) References Cited

U.S. PATENT DOCUMENTS

| 4,588,400 A | * | 5/1986 | Ring et al. .................. 604/304 |
| 4,659,388 A | | 4/1987 | Innami et al. |
| 4,745,058 A | | 5/1988 | Townsly |

FOREIGN PATENT DOCUMENTS

| DE | 2971301 | 2/1998 |
| WO | 9533046 | 12/1995 |

OTHER PUBLICATIONS

Steinkraus, Handbook of Indigenous Fermented Foods, Marcell Dekker, Inc., New York, pp. 486–492, 1996.*

* cited by examiner

Primary Examiner—Francisco Prats
(74) Attorney, Agent, or Firm—Bucknam and Archer

(57) ABSTRACT

Pharmaceutical and alimentary compositions containing *Acetobacter xylinum* as the active ingredient for the treatment of gastroenteral dysmicrobisms, gastroenteral acute and chronic infections and impairments of the gastroenteral functionality.

8 Claims, No Drawings

PHARMACEUTICAL AND ALIMENTARY COMPOSITIONS CONTAINING BACTERIA OF GENUS ACETOBACTER

The present invention relates to pharmaceutical and alimentary compositions containing microorganisms of the genus Acetobacter.

The use of microorganisms such as lactobacilli, *Bacillus subtilis*, Bifidobacteria, Enterococcus or *Streptococcus faecium* in therapy has been established for a long time, such use being connected with studies on the favourable effects deriving from a diet based on yoghurt or other food based on fermented milk.

The microorganisms listed above, either in the form of freeze-dried pure culture or in aqueous suspension, are widely used in the pharmaceutical industry and are the active ingredient of formulations for the treatment of altered intestinal flora connected with pathological conditions or with antibiotic use.

On the other hand, the restoration of the intestinal bacterial flora is a complex problem when considering that the microorganisms present in human intestine are a complex, delicate ecosystem; in each individual, more than 400–500 different bacterial species have been identified.

The composition of the physiological intestinal bacterial flora is relatively constant and the high number of the species present, including both anaerobic and aerobic bacteria, is due to the presence of a number of different sources of carbon and energy which are potentially available in the intestine as a substrate.

The main representatives of the intestinal flora are gram+ anaerobic bacteria, belonging to the genera Bacteroides, Bifidobacterium, Fusobacterium.

aerobic bacteria, among which is the Acetobacter genus, represent only 5–1% of the intestinal microflora.

The equilibrium of the ecosystem is maintained thanks to the action of different factors, among which intestinal peristalsis, secretions, immune factors.

Bacterial flora produces antibacterial and bacteriostatic substances such as cholicins and short-chain fatty acids which prevent colonization by pathogenic microorganisms. The bacterial flora prevents pathogenic microorganisms from adhering to the intestine walls and stimulate peristalsis thereby decreasing the density of the microbial load.

The synergistic action among the different members of the bacterial flora is paramount in exerting a control action which is not only a barrier function, since a close relationship between the intestinal immune system and the microbial mass exists, as evidenced by several studies.

Now it has been found that bacterium *Acetobacter xylinum* is particularly effective for restoring a normal bacterial flora after pathological or iatrogenic impairments or alterations.

Bacteria belonging to the genus Acetobacter are aerobic microorganisms (respiratory metabolism), gram negative, sometimes variable, ellipse- or rod-shaped, catalase positive.

The main characteristic of these bacteria is their capability of oxidizing ethanol to acetic acid.

Most Acetobacter are capable of using as a carbon source different substrates, in addition to ethanol: glucose, lactate, acetate, mannitol. Acetobacter bacteria are microorganisms which can be found on fruit, flowers, alcoholic drinks, and they have never shown a pathogenic activity towards humans, on the contrary they are present in human intestine in physiological conditions. Acetic bacteria have a temperature optimum around 30° C., whereas the optimum pH ranges from 5 to 6.

A further, important characteristic of acetic bacteria is their capability of reproducing even in the presence of antibiotics. Moreover, Acetobacteria can multiply in the intestine thanks to their capability of surviving in the presence of small amounts of $O_2$.

*Acetobacter xylinum* has been used in the paper and cellulose industry, whereas no pharmaceutical uses thereof are known.

Therefore the invention relates to pharmaceutical and alimentary compositions containing *Acetobacter xylinum* as the active ingredient, in admixture with suitable carriers.

The compositions of the invention can be used for the treatment of gastroenteral pathologies such as diarrhoea of various origin, colitis, or for the prevention of the side-effects induced by concomitant treatments with antibiotics due to altered intestinal flora composition.

Compared with the known formulations based on Lactobacilli or anaerobic bacteria, the compositions of the invention have the advantage of a markedly lower effective bacterial load. Doses of $10^4$–$10^5$ bacteria for single dosage are capable of quickly resolving the above cited pathological conditions, whereas doses of $10^6$–$10^9$ bacteria are usually suggested for Lactobacilli and the like.

Moreover, *Acetobacter xylinum* produces, in the presence of glucose, cellulose fibrils which have a favourable effect on intestinal peristalsis. *Acetobacter xylinum* further allows to adjust the intestinal pH thereby preventing the development of pathogenic microorganisms and fungi and favouring the elimination of toxic substances.

*Acetobacter xylinum* strains are available from collections such as ATCC, DSM and Institut Pasteur or can be recovered with known techniques, as described for example in Bergey's Manual of Systematic Bacteriology Williams & Wilkins Pub. Co., Vol. 1, pages 267–269, using suitable substrates and preferably apple juice or juices of other fruits.

The pharmaceutical compositions of the invention can be administered orally or rectally.

For this purpose, suitable formulations are suspensions of bacteria in aqueous carriers, capsules or sachets containing the freeze-dried bacteria, suppositories or microenemas.

Examples of alimentary compositions comprise juices, gelatine, fruit extracts or mousse added with freeze-dried *Acetobacter xylinum* or creams, sauces, dressing and the like.

The following examples illustrate the invention in further detail.

EXAMPLE 1

Capsules containing $10^3$–$10^6$ *Acetobacter xylinum* ATCC 14851 cells freeze-dried on a glucose carrier are prepared, to be administered 2–3 times a day, before meals.

EXAMPLE 2

Concentrated juice fruit ampoules fitted with doser-cap containing $10^3$–$10^6$ cells of *Acetobacter xylinum*.

EXAMPLE 3

Enemas for extemporary preparation mixing *Acetobacter xylinum* cells ($10^3$–$10^6$) and sterile water.

EXAMPLE 4

Suppositories of *Acetobacter xylinum* cells ($10^3$–$10^6$) on a glucose medium and excipients.

What is claimed is:

1. A method of treatment of gastroenteral pathologies, acute infections and impairment of gastroenteral function comprising the oral administration to a patient in need thereof of a pharmaceutical composition containing *Acetobacter xylinum* as the active ingredient.

2. The method as defined in claim 1, wherein said pharmaceutical composition contains $10^3$–$10^6$ cells of *Acetobacter xylinum*.

3. A method of treatment of gastroenteral pathologies, acute infections and impairments of gastroenteral function comprising the rectal adminisration to a patient in need the of a pharmaceutical composition containing *Acetobacter xylinum*.

4. The method as defined in claim 3, wherein said pharmaceutical composition contains $10^3$–$10^6$ cells of *Acetobacter xylinum*.

5. A capsule for oral administration containing a pharmaceutical composition wherein *Acetobacter xylinum* is the active ingredient for the treatment of gastroenteral pathologies, acute infections and impairment of gastroenteral function.

6. The capsule as defined in claim 5, wherein said pharmaceutical composition contains $10^3$–$10^6$ cells of *Acetobacter xylinum*.

7. A suppository for rectal administration containing a pharmaceutical composition wherein *Acetobacter xylinum* is the active ingredient for the treatment of gastroenteral pathologies, acute infections and impairments of gastroenteral function.

8. The suppository as defined in claim 7, wherein said pharmaceutical composition contains $10^{3-10^6}$ cells of *Acetobacter xylinum*.

* * * * *